United States Patent
Robinson et al.

(10) Patent No.: US 10,568,770 B2
(45) Date of Patent: Feb. 25, 2020

(54) CONTROLLED RELEASE IODINE STRUCTURE FOR USE WITH WOUND CARE

(71) Applicant: KCI Licensing, Inc., San Antonio, TX (US)

(72) Inventors: Timothy Mark Robinson, Shillingstone (GB); Brian Andrews, Wimborne (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 74 days.

(21) Appl. No.: 15/571,356

(22) PCT Filed: May 8, 2016

(86) PCT No.: PCT/US2016/031398
§ 371 (c)(1),
(2) Date: Nov. 2, 2017

(87) PCT Pub. No.: WO2016/179575
PCT Pub. Date: Nov. 10, 2016

(65) Prior Publication Data
US 2018/0280200 A1    Oct. 4, 2018

Related U.S. Application Data

(60) Provisional application No. 62/158,321, filed on May 7, 2015.

(51) Int. Cl.
*A61F 13/00* (2006.01)
*A61L 26/00* (2006.01)
(Continued)

(52) U.S. Cl.
CPC .. *A61F 13/00063* (2013.01); *A61F 13/00068* (2013.01); *A61L 15/46* (2013.01);
(Continued)

(58) Field of Classification Search
CPC ......... A61F 13/00063; A61F 13/00068; A61L 15/46; A61L 2300/106; A61L 2300/404;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Hurlow (Advances in Wound Care 2012;1(2):104-107). (Year: 2012).*

(Continued)

*Primary Examiner* — Ernst V Arnold

(57) ABSTRACT

Systems, methods, and apparatuses for generating and releasing iodine are described. Some embodiments may include a dressing member including a plurality of iodine-forming reagents and a water-swellable material. In some embodiments, the dressing member may include water-swellable fibers. The water-swellable fibers may each include a water-swellable material in which iodine-forming reagents are dispersed. As liquid comes into contact with and is absorbed by the water-swellable material, the iodine-forming reagents may come into contact with each other, causing an iodine-forming reaction to occur, producing iodine.

20 Claims, 4 Drawing Sheets

(51) Int. Cl.
*A61L 15/46* (2006.01)
*A61M 1/00* (2006.01)
(52) U.S. Cl.
CPC ........ *A61M 1/0088* (2013.01); *A61M 1/0096* (2014.02); *A61L 2300/106* (2013.01); *A61L 2300/404* (2013.01); *A61L 2300/62* (2013.01)
(58) Field of Classification Search
CPC .............................................. A61L 2300/62; A61M 1/0088; A61M 1/0096
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0249688 A1* | 9/2010 | Ambrosio | A61L 27/52 602/43 |
| 2011/0257572 A1 | 10/2011 | Locke et al. | |
| 2012/0245540 A1* | 9/2012 | Zimnitsky | A61K 31/385 604/319 |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| CN | 203576752 U | 5/2014 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |

(56) References Cited

FOREIGN PATENT DOCUMENTS

| | | | |
|---|---|---|---|
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 0128600 A1 | 4/2001 | |
| WO | 03090800 A1 | 11/2003 | |
| WO | WO-2012092908 A1 * | 7/2012 | ............. A61L 15/28 |

OTHER PUBLICATIONS

Waring et al. Biomaterials 2001;22:903-912) (Year: 2001).*
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
PCT-US2016-031398—Written Opinion dated Aug. 2, 2016.
PCT-US2016-031398—ISR dated Aug. 2, 2016.
European Examination Report for corresponding Application No. 16724555.4, dated Sep. 4, 2019.

\* cited by examiner

CONTROLLED RELEASE IODINE STRUCTURE FOR USE WITH WOUND CARE

TECHNICAL FIELD

This disclosure relates generally to medical treatment systems for treating tissue sites and processing fluids. More particularly, but not by way of limitation, the disclosure relates to a dressing capable of generating and distributing iodine to a tissue site. The dressing may be used with or without reduced pressure to treat a tissue site.

BACKGROUND

Iodine and iodine solutions have been proven to have effective antiseptic properties against pathogens. Iodine is commonly used as a skin cleanser and antiseptic in preoperative hand scrubs. Early solutions of iodine were known to have side effects, including irritation and/or staining of skin. These side effects were generally associated with the relatively high iodine concentration of the solutions delivered to the skin. To reduce and control the dosage of iodine delivered to the skin site, iodophors were developed, which are essentially water-soluble continuous phases that contain the iodine, which is only released when water solubilizes the continuous phase.

However, in all of the water-soluble systems containing iodine, the carrier or continuous phase becomes mobile upon contact with water, and may block or hinder the removal of wound fluids in negative-pressure wound dressings. In addition, if a highly-exuding wound is encountered, or additional fluid (saline) is added to a wound as part of a cleaning or irrigation operation, a high dosage of iodine may be released, which may be undesirable. Furthermore, the water-soluble dressings may also be rather cumbersome and messy upon removal and can prove difficult to handle and contain. Additionally, given that elemental iodine is effectively stored within the dressing, storage risks or hazards may be posed.

Thus, while the benefits of using iodine solutions as antiseptics in the medical context are known, the complexity of treating wounds can be a limiting factor, particularly when combined with negative-pressure therapy.

BRIEF SUMMARY

The disclosure provides a dressing member for treating a tissue site. The dressing member provides iodine to the tissue site. According to an illustrative embodiment, a dressing member for treating a tissue site may include a plurality of iodine-forming reagents and a covering material. The plurality of iodine-forming reagents may be dispersed in the dressing member and adapted to react to form iodine. The covering material may encapsulate each of the iodine-forming reagents. The plurality of iodine-forming reagents may be coated with varying thicknesses of the covering material. The dressing member may also include a carrier material. The covering material of the dressing member may be further adapted to absorb fluid and to release the iodine-forming reagents, wherein the fluid may be a wound exudate from the tissue site, a saline solution, or water. The covering material may include a water-swellable material or a water-soluble material. The covering material may also include a mixture of water-swellable and water-soluble materials. The water-swellable material may form one or more water-swellable fibers, and the water-soluble material may form one or more water-soluble beads. The water-soluble beads may include water-sensitive polymers, which may be polyvinyl alcohol or polyvinyl pyrrolidone. The water-soluble beads may also include a coating that includes a biodegradable matrix. The biodegradable matrix may be formed from a glass, a ceramic, sodium phosphates, apatites, or polymers, which may be a caprolactam or a lactate. The covering material of the dressing member may further include an indicator for detecting the release of iodine, which may be a starch. The plurality of iodine-forming reagents may include an iodide salt and an iodate salt. The iodide salt may be potassium iodide (KI), and the iodate salt may be potassium iodate ($KIO_3$). The iodine produced from the dressing member may be released over differing time periods. The water-swellable fibers may be in the form of hollow fibers, and two or more hollow fibers may be combined, for example by twisting, to form a yarn where the first hollow fiber may contain a first iodine-forming reagent and the second hollow fiber may contain a second iodine-forming reagent. Two or more yarns are bundled or twisted together to form a woven or a non-woven matrix. The water-swellable material may include a gelatine or a gelatine/carbohydrate blend, and the carbohydrate may be a cellulose derivative such as carboxymethyl cellulose (CMC).

According to another illustrative embodiment, a system for treating a tissue site may include a manifold, a dressing member, a drape, and a reduced-pressure interface. The manifold may be adapted to receive reduced pressure and distribute the reduced pressure to the tissue site. The dressing member may be adapted to form a sealed space around the tissue site and manifold, and may include a plurality of iodine-forming reagents and a covering material. The drape may be adapted to cover the dressing member. The reduced-pressure interface may be adapted to deliver reduced pressure and may be in fluid communication with the sealed space and the manifold. The system may further include a reduced-pressure source in fluid communication with the reduced-pressure interface. The manifold may be an open-cell, reticulated polyurethane foam, and may include at least one material selected from the group of polyurethane foam, polyvinyl alcohol foam, polyethylene foam, expanded polytetrafluoroethylene, silicone foam, loofa sponge, sea sponge, gauze, and felted mats. The system may further include a reduced-pressure delivery tube fluidly connected to the reduced-pressure interface for delivering a reduced pressure to the tissue site.

According to yet another illustrative embodiment, a method of manufacturing a dressing member may include providing a plurality of iodine-forming reagents adapted to react with each other to form iodine and coating the plurality of iodine-forming reagents with a covering material. The method may further include disposing the plurality of coated iodine-forming reagents in a carrier material. The covering material may include a water-swellable material or a water-soluble material. The water-swellable material may be formed from gelatine or gelatine/carbohydrate blends, wherein the carbohydrate may be a cellulose derivative such as carboxymethyl cellulose (CMC). The plurality of iodine-forming reagents may include an iodide salt and an iodate salt, where the iodide salt may be potassium iodide (KI) and the iodate salt may be potassium iodate ($KIO_3$). The method may further include twisting a first hollow fiber containing a first iodine-forming reagent with a second hollow fiber containing a second iodine-forming reagent to form a combined yarn. The hollow fibers may be formed by electrospinning. The method may further include bundling or twisting together the combined yarn to form a woven or non-woven matrix.

According to yet another illustrative embodiment, a system for treating a tissue site may include a dressing member, a drape, and a reduced-pressure interface. The dressing member may be adapted to be disposed proximate the tissue site and may include a carrier material and a plurality of iodine-forming reagents. The iodine-forming reagents may be adapted to react to produce iodine. The drape may be adapted to cover the dressing member. The reduced-pressure interface may be adapted to deliver reduced pressure and may be in fluid communication with the dressing member.

According to still another illustrative embodiment, a method for treating a tissue site may include applying a dressing member adjacent to the tissue site and providing iodine formed from the dressing member to the tissue site. The iodine may be released over a length of time. The plurality of reagents may include an iodide salt and an iodate salt. The method may further include providing a starch in the dressing member, wherein the starch is adapted to form a blue-black color when exposed to iodine. Additionally, the method may further include applying reduced pressure to the tissue site. The reduced pressure may be applied to the tissue site prior to the application of the dressing member, subsequent to the application of the dressing member, or while the dressing member is applied to the tissue site.

Other aspects, features, and advantages of the illustrative embodiments will become apparent with reference to the drawings and detailed description that follow.

DESCRIPTION OF EXAMPLE EMBODIMENTS

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims.

The disclosed iodine-forming dressing members can overcome shortcomings of previous iodine-containing wound dressings by generating iodine after being applied to a tissue site and in response to coming into contact with wound fluids such as wound exudates. The iodine-forming dressing members disclosed herein provide controlled release of iodine. In one embodiment, iodine-forming dressing members provide a low-level release of iodine, which may prevent a high and/or uncontrolled dose of iodine from being released. Additionally, the iodine-forming dressing members in the present disclosure may be easily removed and discarded. Furthermore, storage risks associated with elemental iodine may be reduced or even eliminated.

Figure 1:
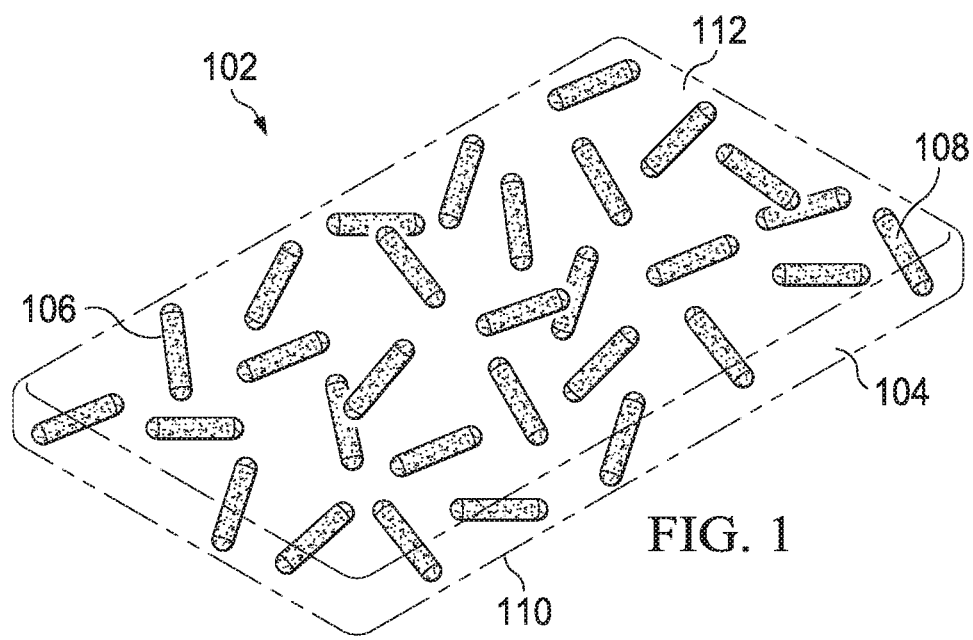
FIG. 1 is a schematic diagram of an illustrative embodiment of an iodine-forming dressing member.

FIG. 1 is a schematic diagram of an exemplary embodiment of an iodine-forming dressing member 102. The iodine-forming dressing member 102 may include a carrier material and a plurality of iodine-forming reagents coated by a covering. For example, as illustrated in FIG. 1, the iodine-forming reagents 108 may be encapsulated by a covering material in fibers 106. The carrier material 104 may be fluid permeable and may provide a substantially sheet-like structure for the iodine-forming dressing member 102. The fibers 106 may, for example, be dispersed throughout the carrier material 104. The covering may be adapted to absorb moisture, such as exudate from a tissue site, by drawing or wicking the fluid from a peripheral surface 110 towards an external surface 112 of the iodine-forming dressing member 102. In some embodiments, for example, the fibers 106 may be water-swellable fibers.

In one embodiment, the carrier material 104 may be comprised of any substantially pure hydrophobic material and may have a variety of structures, including materials and structures that allow fluid, e.g., liquid or gas, to pass through the carrier material 104 without being absorbed by the carrier material 104. As defined herein, a hydrophobic material that is substantially pure will be substantially free of hydrophilic components due to the tendency for hydrophilic materials to retain fluid. The carrier material 104, for example, may comprise a hydrophobic elastomer, such as a hydrophobic silicone elastomer. The hydrophobic characteristics of the carrier material 104 may prevent the carrier material 104 from directly absorbing fluid, such as exudate, from a tissue site, but may allow the fluid to pass through. Thus, the carrier material 104 may permit the passage of fluid away from the peripheral surface 110 to allow the fluid to come into contact with the fibers 106.

The carrier material 104 may have any size, shape, or thickness depending on a variety of factors, such as the type of therapy being implemented or the nature of a tissue site or the peripheral surface 110. The thickness of the carrier material 104 may be increased or decreased to optimize the effectiveness of the carrier material 104 as a separator between a tissue site and the plurality of iodine-forming reagents 108. The thickness of the carrier material 104 may also be adjusted according to a desired ratio of hydrophobic carrier material to iodine-forming reagents 108, depending on the application.

For example, in the example embodiment of FIG. 1 in which the plurality of iodine-forming reagents 108 are encapsulated by the fibers 106, a thicker carrier material 104 may be desirable to restrain or prevent the fluid from contacting the tissue site or peripheral surface 110 in applications in which a tissue site releases a large amount of fluid. Conversely, a thinner carrier material 104 may be desirable in applications in which a lower amount of fluid is present. For example, the carrier material 104 may be between about 50 to 2000 micrometers in thickness.

Figure 2:
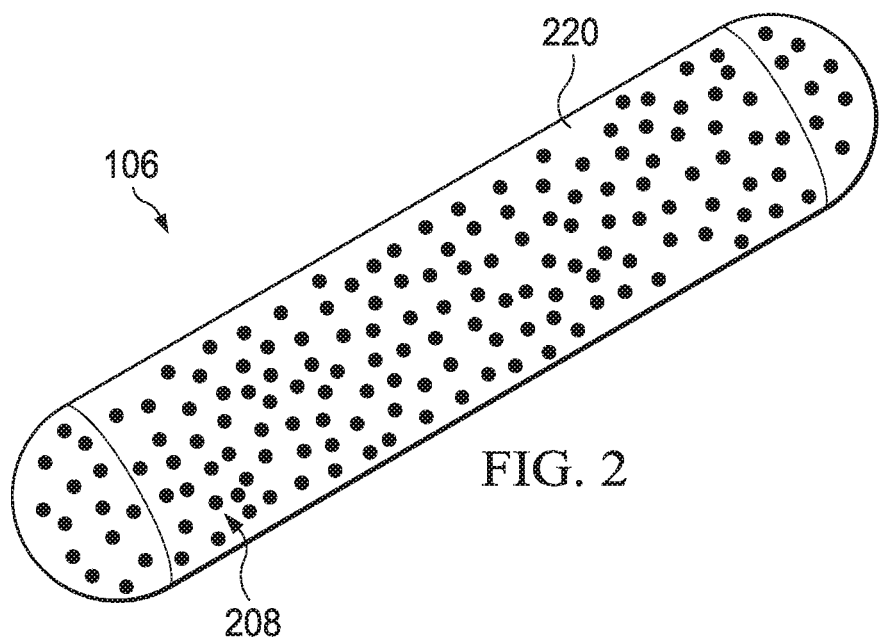
FIG. 2 is a sectional schematic diagram of an iodine-forming fiber of the iodine-forming dressing member of FIG. 1.

FIG. 2 is a sectional schematic diagram of an example embodiment of the fiber 106, illustrating additional details that may be associated with some embodiments. The fiber 106 may include multiple components. For example, in the embodiment of FIG. 2, the fiber 106 may include a water-swellable material 220. A plurality of iodine-forming reagents 208 may be dispersed within the fiber 106.

The water-swellable material 220 may be a material capable of absorbing fluid. The water-swellable material 220 may be substantially formed into fibers, such as the fiber 106. The fibers, such as the fiber 106, may be a hollow fiber formed by extrusion from a melt or solution, as could be achieved through electrospinning, which involves using a high voltage to create an electrically-charged jet of solution or melt, which may dry or solidify to produce a fiber. In other embodiments, the water-swellable material 220 may be formed into a yarn or a sheet-like layer. In one embodiment, the water-swellable material 220 may be formed from gelatin or gelatin/carbohydrate blends, where the carbohydrate may be a cellulose derivative such as carboxymethyl cellulose (CMC).

The plurality of iodine-forming reagents 208 may include an iodide salt reagent and an iodate salt reagent. The iodine-forming reagents 208 may react according to the following general chemical equation:

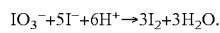

$$IO_3^- + 5I^- + 6H^+ \rightarrow 3I_2 + 3H_2O.$$

In accordance with this chemical equation, $IO_3^-$ represents an iodate reagent, and $5I^-$ represents an iodide reagent. In some embodiments, the iodide salt reagent may be potassium iodide (KI), and the iodate salt reagent may be potassium iodate ($KIO_3$).

In the exemplary embodiment of FIG. 2, the fiber 106 may include the iodide salt reagent or the iodate salt reagent. In such embodiments, the iodine-forming dressing member 102, may include a first portion of fibers that may encapsulate the iodide salt reagent and a second portion of the fibers that may encapsulate the iodate salt reagent. In other embodiments, a fiber may include both types of the iodine-forming reagents 208, for example the iodide salt reagent and the iodate salt reagent.

Referring now to FIGS. 1 and 2, when the fibers 106 are dispersed in the carrier material 104, the water-swellable material 220 of the fibers 106 may be in fluid contact with the carrier material 104. The water-swellable material 220 may provide an absorption gradient to draw or otherwise wick fluid away from a tissue site. Fluid from a tissue site may be drawn by the absorption gradient through the carrier material 104 and then absorbed by the water-swellable material 220. The water-swellable material 220 may retain or bond to the fluid in conjunction with a physical or chemical change to the water-swellable material 220. The water-swellable material 220 may, for example, gel, increase in viscosity, or otherwise thicken upon contact with fluid from a tissue site, thereby trapping the fluid.

The wicking properties of the water-swellable material 220 may help to quickly draw fluid, e.g., exudate, away from a tissue site, and thus may prevent the accumulation of fluid at or near the tissue site. In a similar manner, the carrier material 104 may facilitate the evaporation of fluid absorbed by the water-swellable material 220 or otherwise transferred through the carrier material 104 towards the external surface 112 of the iodine-forming dressing member 102. Since fluid from a tissue site passes through the carrier material 104 to reach the water-swellable material 220 as described above, the carrier material 104 may provide a separation between a tissue site and the water-swellable material 220, i.e., the carrier material 104 may be positioned between the peripheral surface 110 of the iodine-forming dressing member 104 and the water-swellable material 220.

Figure 3:
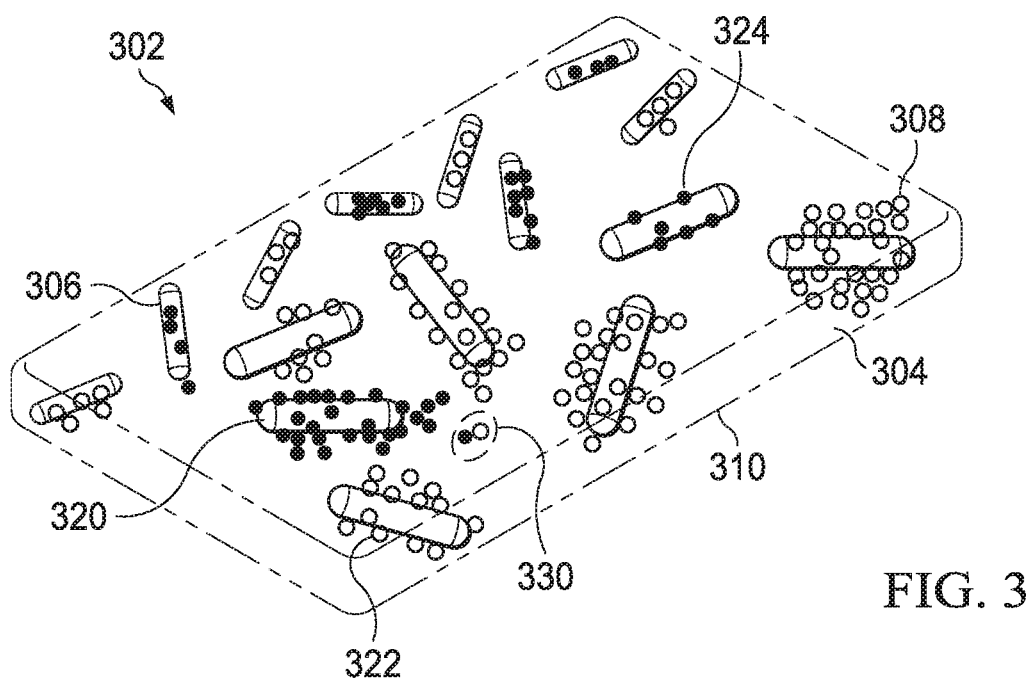
FIG. 3 is a schematic diagram of another illustrative embodiment of an iodine-forming dressing member.

FIG. 3 illustrates another embodiment of an iodine-forming dressing member 302 in which the iodine-forming reagents 308 may be released from the water-swellable fibers 306 in response to the presence of fluid, such as wound fluid, in the iodine-forming dressing member 302. In operation, wound fluid, such as wound exudates, may enter the iodine-forming dressing member 302 through the peripheral surface 310. As the wound fluid travels through the carrier material 304, the wound fluid comes into contact with the water-swellable fibers 306. Upon contact with the water-swellable fibers 306, the fluid may be absorbed by the water-swellable material 320, and therefore cause the water-swellable fibers 306 to enlarge or swell as they contain an increasing volume of fluid. Upon swelling to a specified degree, the iodine-forming reagents 308 encapsulated by the water-swellable fibers 306 may begin to come into contact with the absorbed fluid, and as a result, be released from the water-swellable fibers 306 into the surrounding carrier material 304. As the water-swellable fibers 306 continue to absorb fluid and swell to an increasing size, an increasing amount of the iodine-forming reagents 308 may be released into the carrier material 304.

Still referring to FIG. 3, as the iodine-forming reagents 308 are released into the carrier material 304, the reagents previously contained by different water-swellable fibers 306 may come into contact with each other. For example, as the water-swellable fibers 306 swell, the iodide salt reagent 322 may be released from some of the water-swellable fibers 306 into the carrier material 304, and iodate salt reagent 324 may be released from other of the water-swellable fibers 306 into the carrier material 304. As the iodide salt reagent 322 and the iodate salt reagent 324, collectively referred to as the iodine-forming reagents 308, come into contact with each other in the carrier material 304, an iodine-forming reaction 330 may occur, producing iodine. This iodine may then migrate out of the iodine-forming dressing member 302 and towards a tissue site. The generated iodine from the iodine-forming reaction 330 may perform anti-bacterial therapeutic effects at the tissue site as well as in a dressing applied to the tissue site, for maintaining a clean or disinfected dressing. The water-swellable fibers 306 may not dissolve, thus substantially retaining their form and permitting the iodine-forming dressing member 302 to be removed intact.

In other embodiments, the iodine-forming reaction 330 may not occur in the carrier material 304. For example, the released iodide salt reagent 322 and iodate salt reagent 324 may be released into the carrier material 304 and travel out of the iodine-forming dressing member 302 and into another structure, such as a manifold, before coming into contact with each other to result in an iodine-forming reaction. In some embodiments, the released iodide salt reagent 322 and the released iodate salt reagent 324 may further travel to a tissue site before coming into contact with each other to cause an iodine-forming reaction to occur.

Figure 4:
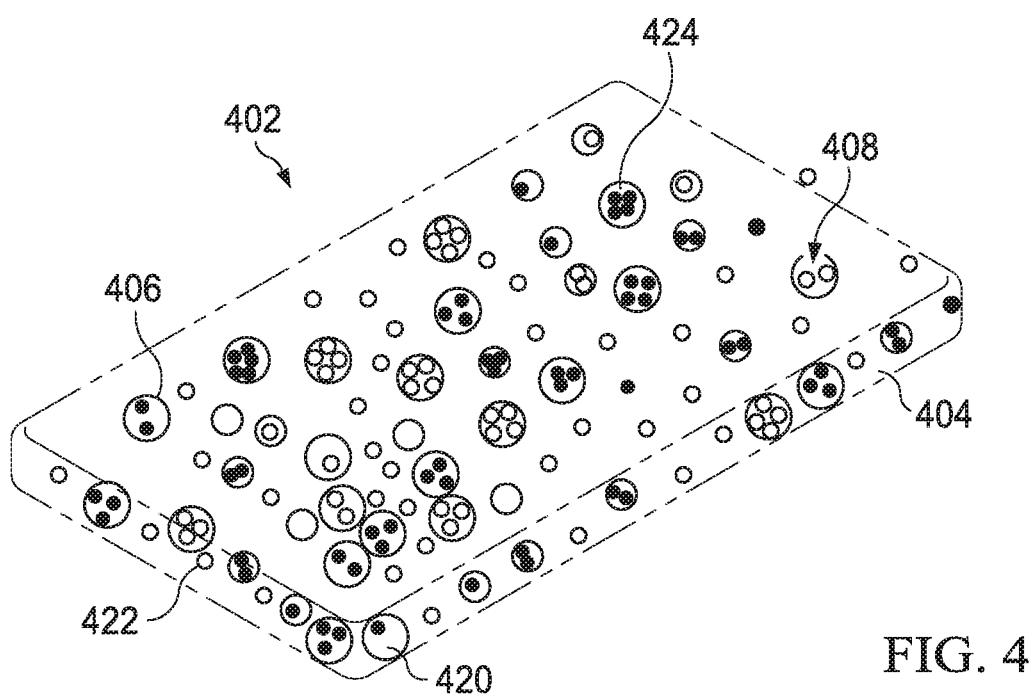
FIG. 4 is a schematic diagram of another illustrative embodiment of an iodine-forming dressing member.

FIG. 4 illustrates another embodiment of an iodine-forming dressing member 402, in which water-soluble beads 406 may be used to contain the plurality of iodine-forming reagents 408, such as the iodide salt reagent 422 and the iodate salt reagent 424. The water-soluble beads 406 may be formed from a water-sensitive material 420. The water-sensitive material 420 may include water-sensitive polymers, such as polyvinyl alcohol or polyvinyl pyrrolidone. The water-sensitive material 420 may also include other polymers, such as carboxymethyl cellulose (CMC) and CMC salts, alginates and gums such as xanthates, guar, and carrgeenan, hydrophilic polyurethanes and acrylics, and polyethylene oxides. The water-soluble beads 406 may have any size or shape, depending on a variety of factors including the amount of fluid anticipated to be released by a tissue site. This specification contemplates embodiments including a mixture of water-soluble beads 406 with varying thicknesses of water-sensitive material 420 containing the iodine-forming reagents 408, to allow for a time-controlled delivery of the iodine-forming reagents 408. For example, the greater the amount of water-sensitive material 420 containing the iodine-forming reagents 408, the longer it may take for fluid to reach the iodine-forming reagents 408 and for the iodine-forming reagents 408 to be released for the production of iodine. As a result of increasing the amount of water-sensitive material 420 in some of the water-soluble beads 406, some of the water-soluble beads 406 may be significantly larger than others in this embodiment.

In other embodiments, to provide for a slower release of the iodine-forming reagents 408, the water-soluble beads 406 may also be coated with a biodegradable matrix. In some embodiments, the biodegradable matrix may be formed from glass or ceramic, for example bioglass, sodium phosphates and apatites, or polymers, for example caprolactams and lactates. Other suitable polymers may include starches, polyglycolic acid, cellulose, and chitosan.

In order to allow for a wide range of controlled iodine release levels over time, other embodiments of iodine-forming dressing members may include a mixture of water-swellable and water-soluble materials for encapsulating the iodine reagents. As previously discussed, water-soluble materials may include, among others, CMC salts, xanthan gum, guar gum, polyvinyl alcohols, polyethylene oxides, and polyvinyl pyrrolidones. In some embodiments, the water-soluble fractions will enable a higher dose of iodine to be formed by and released from the iodine-forming dressing member. Including a mixture of water-swellable and water-soluble materials may also allow for a variety of dressing integrity options, which may be tailored to the particular application and/or therapy involved.

Figure 5:
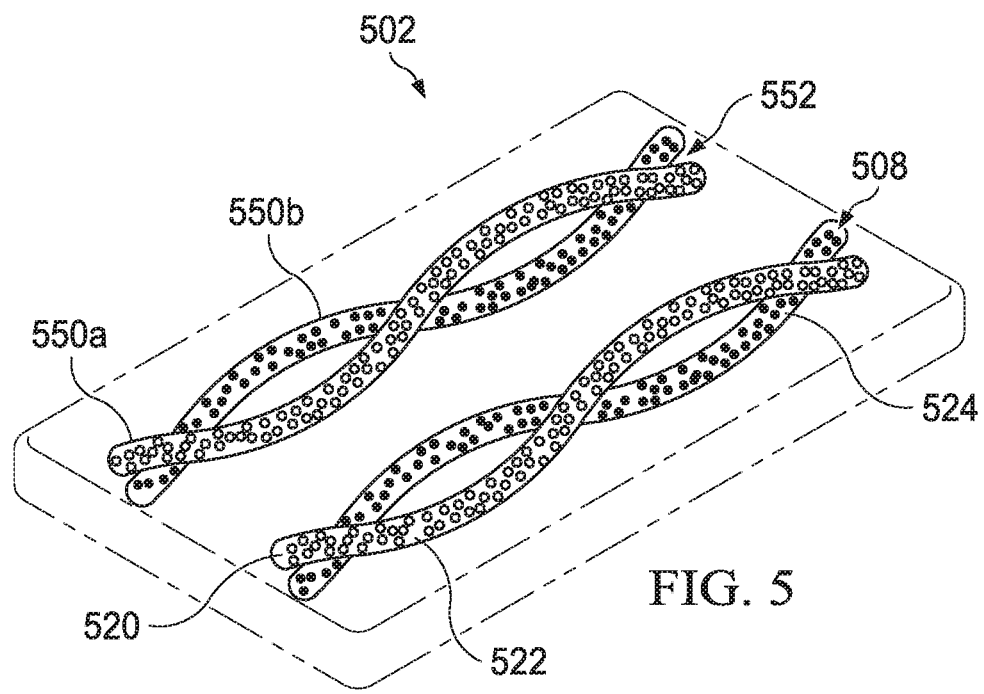
FIG. 5 is a schematic diagram of another illustrative embodiment of an iodine-forming dressing member.

FIG. 5 illustrates another embodiment of an iodine-forming dressing member 502 in which the iodine-forming reagents 522 and 524 are encapsulated in long fibers, such as the iodide salt fibers 550a and the iodate salt fibers 550b, collectively the iodine reagent fibers 550. The iodide salt fibers 550a and the iodate salt fibers 550b may be intertwined to form an iodine-forming yarn 552. Intertwining the iodine reagent fibers 550 maximizes the mixing of the iodine-forming reagents 522 and 524, the iodide salt reagent 522 and the iodate salt reagent 524, in the correct ratio. For example, because the iodine-forming yarn 552 is constructed from both a single iodide salt fiber 550a and a single iodate salt fiber 550b, and assuming that each fiber contains roughly a similar amount of respective iodine-forming reagent, the amount of iodine formed in the iodine-forming dressing member 502 may be maximized per amount of iodine-forming reagents 522 and 524, without leaving excess residual iodine-forming reagents 522 and 524 in the iodine-forming dressing member 502 or at a tissue site.

In some embodiments, the iodine-forming dressing member 502 may include strands of iodine-forming yarn 552, where the iodine reagent fibers 550 vary in thickness. For example, the iodine-forming reagents 508 may be encapsulated in iodine reagent fibers 550, which have differing amounts, and therefore thicknesses, of water-swellable material 520. By varying the thickness of the water-swelling material 520, the dosage of the produced iodine may be released over differing time periods. For example, as fluid from a tissue site is absorbed by the water-swellable material 520 of the iodine reagent fibers 550 which contain less water-swelling material 520, the absorbed fluid may more quickly mobilize the iodine-forming reagents 522 and 524. Contrarily, iodine reagent fibers 550 which contain a greater amount of water-swelling material 520 may delay the absorbed wound fluid from mobilizing the iodine-forming reagents 522 and 524. This configuration ensures that the beneficial effects of the iodine are delivered for a continuous period of time. Such a controlled time release may not otherwise be the case if all iodine reagent fibers 550 have the same amount, and therefore thickness, of water-swellable material 520, as a majority of the iodine may be released from the fibers simultaneously. In some embodiments, strands of iodine-forming yarn 552 with iodine reagent fibers 550 having different thicknesses of water-swellable material 520 will be evenly distributed about the structure, however this does not necessarily have to be the case. For example, depending on the type of wound or tissue site, strands of iodine-forming yarn 552 with iodine reagent fibers 550 having lesser thicknesses of water-swellable material 520 may be placed towards the edges of the dressing member 502. Such a configuration may result in more quickly delivering a greater amount of therapeutic iodine to the most severe, or deepest, portions of a wound or tissue site.

Figure 6:
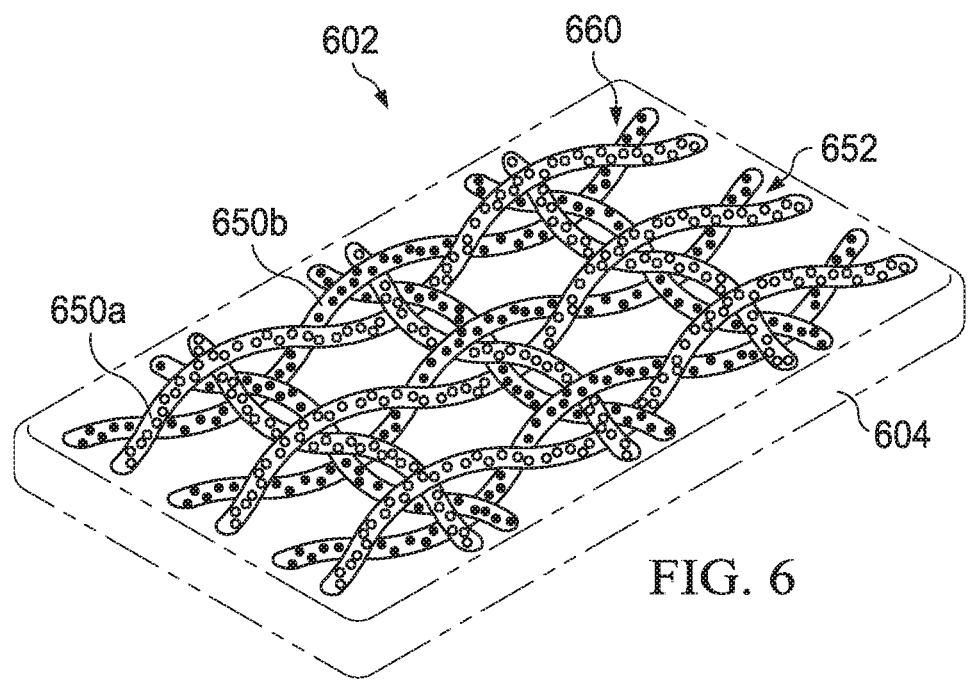
FIG. 6 is a schematic diagram of another illustrative embodiment of an iodine-forming dressing member.

FIG. 6 illustrates another embodiment of an iodine-forming dressing member 602 in which strands of iodine-forming yarn 652 may be bundled or twisted together to form a matrix 660. The iodine-forming yarn 652 may include iodide salt fibers 650a and iodate salt fibers 650b, collectively the iodine reagent fibers 650. The matrix 660 may be a woven or non-woven matrix. While numerous configurations of the iodine-forming yarn 652 may be possible, this embodiment may include strands of iodine-forming yarn 652 that were woven together to form a woven matrix 660. The woven matrix 660 may include strands of the iodine-forming yarn 652 arranged along both the length and width of the iodine-forming dressing member 602. For example, in some embodiments, the strands of the iodine-forming yarn 652 may be placed within a carrier material 604. Further, in some embodiments, as the strands of the iodine-forming yarn 652 are woven together, a sheet-like material may be formed. The iodine-forming dressing member 602 may further include multiple sheet-like layers of the woven matrix 656, with the number of layers being tailored to the amount of iodine necessary for the particular type of wound or tissue site.

Figure 7:
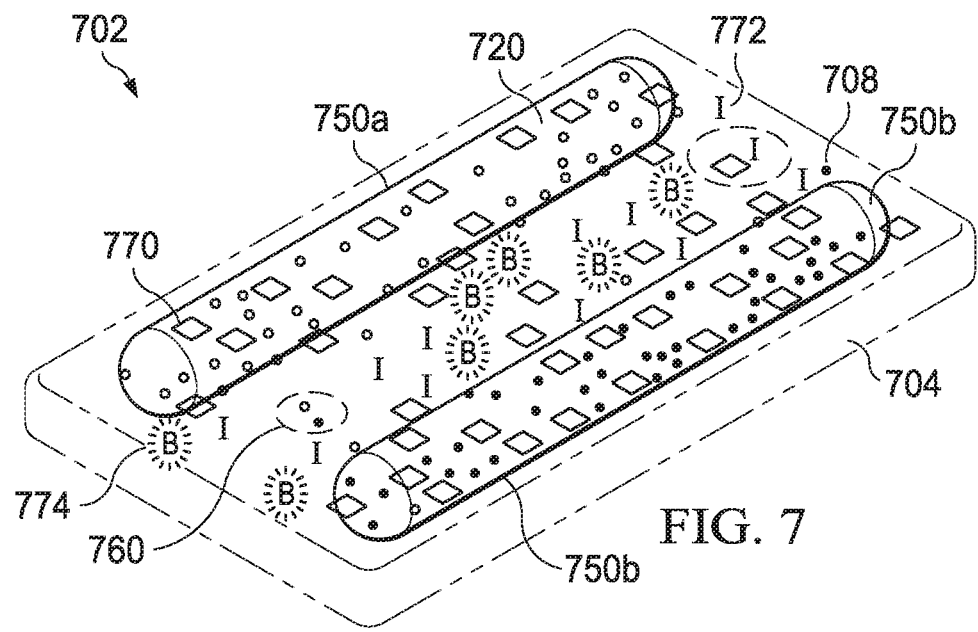
FIG. 7 is a schematic diagram of another illustrative embodiment of an iodine-forming dressing member.

FIG. 7 illustrates another embodiment of an iodine-forming dressing member 702 in which a color indicator, such as starch 770 is added to the water-sensitive or biodegradable coating material 720 of the iodine-reagent fibers 750 for the purpose of signaling the presence of formed iodine 772. For example, in some embodiments, when the iodine-forming reagents 708 are released from the iodine reagent fibers 750, the iodine-forming reaction 760 may occur to form iodine 772. By including a low level of starch, such as starch 770 in the water-sensitive or biodegradable coating material 720, a reaction between the formed iodine and the starch may take place to produce a strong blue-black color 774. The appearance of the blue-black color 774 may indicate that iodine 772 is being released into the carrier material 704 of the iodine-forming dressing member 702 and that the iodine is being released from the iodine-forming dressing member 702. In other embodiments, a color indicator, such as starch 770, may be added to a water-swellable material included in an iodine-forming dressing member.

Iodine-forming dressing members, such as the iodine-forming dressing members in FIGS. 1-7 can have many beneficial or advantageous applications. For example, an iodine-forming dressing member may be particularly advantageous for treating wounds with reduced pressure. Treatment of wounds or other tissue with reduced pressure may be commonly referred to as "reduced-pressure therapy," but is also known by other names, including "negative-pressure wound therapy," "negative-pressure therapy," "vacuum therapy," and "vacuum-assisted closure," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

Figure 8:
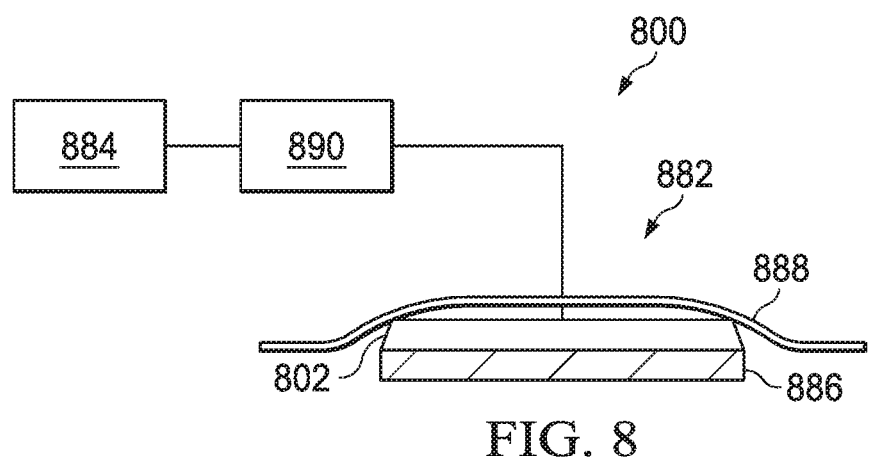
FIG. 8 is a functional block diagram illustrating a reduced-pressure therapy system that may be associated with some embodiments of an iodine-forming dressing member.

FIG. 8 is a schematic diagram of an example embodiment of a reduced-pressure therapy system 800 that may include an iodine-forming dressing member. For example, the reduced-pressure therapy system 800 may include a dressing 882, which can be positioned proximate to a tissue site, and a reduced-pressure source 884 for providing reduced pressure to the dressing 882. In some embodiments, the dressing 882 may include a manifold 886, an iodine-forming dressing member 802, and a drape 888. The iodine-forming dressing member 802 may incorporate any combination, in whole or in part, of suitable features, structures, or elements of the iodine-forming dressing members described herein. For example, the iodine-forming dressing member 802 may incorporate the fibers 106, the water-soluble beads 406, the iodine reagent fibers 550, the matrix 660, the iodine reagent fibers 750, or any suitable combination of features of these embodiments. Alternatively, any combination of suitable features, structures, or elements of the iodine-forming dressing members described herein, such as the fibers 106, the water-soluble beads 406, the iodine reagent fibers 550, the matrix 660, or the iodine reagent fibers 750, may be incorporated in the manifold 886 of the dressing 882 instead of or in addition to the iodine-forming dressing member 802. For example, in certain embodiments, the iodine-forming reagents may be incorporated in the manifold 886 and the iodine-forming dressing member 802 may be omitted. The dressing 882 may be fluidly coupled to the reduced-pressure source 884. The reduced-pressure therapy system 800 may also include an exudate container, such as container 890, coupled to the dressing 882 and to the reduced-pressure source 884.

The term "tissue site" may refer to a wound or defect located on or within a tissue, including without limitation, bone tissue, adipose tissue, muscle tissue, neural tissue, dermal tissue, vascular tissue, connective tissue, cartilage, tendons, or ligaments. A tissue site may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

A reduced-pressure source, such as the reduced-pressure source 884, may be a reservoir of air at a reduced pressure, or may be a manually or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure may be a rough vacuum between about −5 mm Hg (−667 Pa) and about −500 mm Hg (−66.7 kPa). In some embodiments, the pressure may be between about −75 mm Hg (−9.9 kPa) and about −300 mm Hg (−39.9 kPa).

In general, exudates and other fluids may flow toward lower pressure along a fluid path. Further, fluids may be attracted to flow through permeable materials along a path of increasing hydrophilicity or absorbency among the materials. Thus, the term "downstream" may refer to components that are further along a fluid path than components that may be referred to as "upstream." Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

"Reduced pressure" may refer to a pressure less than a local ambient pressure, such as the ambient pressure in a local environment external to a sealed therapeutic environment. The local ambient pressure may also be the atmospheric pressure at which a patient is located. Further, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The components of the reduced-pressure therapy system 800 may be coupled directly or indirectly. Components may be fluidly coupled to each other to provide a path for transferring fluids (for example, liquid and/or gas) between the components. In some exemplary embodiments, components may be fluidly coupled with conduits, such as tubes. A "tube," as used herein, may refer to a pipe, hose, conduit, or other elongated structure with one or more lumina adapted to convey fluids between two ends. In some exemplary embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

The manifold 886 may be adapted to be in fluid communication with a tissue site, the iodine-forming dressing member 802, and the drape 888. For example, the manifold 886 may be placed within, over, on, or otherwise proximate to a tissue site. The iodine-forming dressing member 802 may be placed between the tissue site or the manifold 886 and the drape 888. The drape 888 may be placed over the manifold 886 and the iodine-forming dressing member 802 and sealed to tissue proximate to the tissue site. The tissue proximate to the tissue site may be undamaged epidermis peripheral to the tissue site. Thus, the dressing 882 can provide a sealed therapeutic environment proximate to the tissue site, substantially isolating the tissue site from the external environment. The reduced-pressure source 884 can reduce the pressure in the sealed therapeutic environment. Reduced pressure applied uniformly through the manifold 886 in the sealed therapeutic environment can induce macrostrain and microstrain in the tissue site, as well as remove exudates and other fluids from the tissue site.

In some embodiments, the manifold 886 may be adapted to contact a tissue site. The manifold 886 may be partially or fully in contact with a tissue site. If a tissue site extends into tissue from a tissue surface, for example, the manifold 886 may partially or completely fill the tissue site. In other exemplary embodiments, the manifold 886 may be placed over a tissue site. The manifold 886 may take many forms, and may have many sizes, shapes, or thicknesses depending on a variety of factors, such as the type of treatment being implemented or the nature and size of the tissue site. For example, the size and shape of the manifold 886 may be adapted to the contours of deep and irregular shaped tissue sites.

The manifold 886 may comprise a substance or structure adapted to distribute reduced pressure across a tissue site, remove fluids from across a tissue site, or both. In some exemplary embodiments, the manifold 886 may also facilitate delivering fluids across a tissue site, for example, if a fluid path is reversed or a secondary fluid path is provided. The manifold 886 may include flow channels or pathways that distribute fluids provided to and removed from a tissue site around the manifold 886. In one exemplary embodiment, the flow channels or pathways may be interconnected to improve distribution of fluids provided to or removed from a tissue site. For example, cellular foam, open-cell foam, porous tissue collections, and other porous material, such as gauze or felted mat may include structural elements arranged to form flow channels. Liquids, gels, and other foams may also include or be cured to include flow channels configured to distribute fluid across a tissue site.

In one exemplary embodiment, the manifold 886 may be a porous foam material having interconnected cells or pores adapted to distribute reduced pressure across a tissue site in a substantially uniform manner. The foam material may be either hydrophobic or hydrophilic. In one non-limiting example, the manifold 886 can be an open-cell, reticulated polyurethane foam such as GranuFoam® dressing available from Kinetic Concepts, Inc. of San Antonio, Tex.

In an example embodiment in which the manifold 886 may be made from a hydrophilic material, the manifold 886 may also wick fluid away from the tissue site, while continuing to distribute reduced pressure to the tissue site. The wicking properties of the manifold 886 may draw fluid away from the tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The manifold 886 may further promote granulation at the tissue site when pressure within the sealed therapeutic environment is reduced. For example, any or all of the surfaces of the manifold 886 may have an uneven, coarse, or jagged profile that can induce microstrains and stresses at the tissue site when reduced pressure is applied through the manifold 886 to a tissue site.

In one exemplary embodiment, the manifold 886 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold 886 may further serve as a scaffold for new cell-growth, or a scaffold material may be used in conjunction with the manifold 886 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 888 is an example of a sealing member. A sealing member may be constructed to provide a fluid seal between two components or two environments, such as between a therapeutic environment and a local external environment. The sealing member may be, for example, an impermeable or semi-permeable, elastomeric film that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion of, or an entirety of the sealing member. Other exemplary embodiments of an attachment device may include a double-sided tape, paste, hydrocolloid, hydrogel, silicone gel, organogel, or an acrylic adhesive.

In some embodiments, the reduced pressure developed by the reduced-pressure source 884 may be delivered through a tube to a connector. The connector may be a device configured to fluidly couple the reduced-pressure source 884 to the sealed therapeutic environment formed by the drape 888. In some embodiments, the connector may include a flange portion that couples to the drape 888 and a port portion that fluidly couples to the tube. In one exemplary embodiment, the connector may be a T.R.A.C.® Pad or Sensa T.R.A.C.® Pad available from Kinetic Concepts, Inc. of San Antonio, Tex. In other exemplary embodiments, the connector may also be a conduit inserted through the drape 888. The connector allows the reduced pressure to be delivered to the sealed therapeutic environment between the drape 888 and the tissue site. In some embodiments, the connector may extend through the drape 888 to the iodine-forming dressing member 802, but numerous arrangements are contemplated. The connector can deliver the reduced pressure through the drape 888 of the dressing 882 to the manifold 886.

The iodine-forming dressing member 802 is also preferably permeable to gases. For example, in some embodiments, the iodine-forming dressing member 802 may include fibers 106. Reduced pressure may be transferred with and through spaces or voids between the fibers 106 in such embodiments of the iodine-forming dressing member 802.

The container 890 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with reduced-pressure therapy. Some exemplary embodiments of the reduced-pressure therapy system 800 may not include the container 890; instead, these exemplary embodiments of the therapy system 800 handle fluid storage with the dressing 882.

In operation, the reduced-pressure source 884 may supply reduced pressure to the dressing 882, including the manifold 886, and ultimately a tissue site. The reduced pressure source may draw fluids out of the tissue site, and the manifold 886 may distribute the fluids from the tissue site to the dressing 882. Upon reaching the dressing 882, the fluids may come into contact with and travel into the iodine-forming dressing member 802. Upon entry into the iodine-forming dressing member 802, the fluids may be absorbed by water-swellable material, which may be included in the fibers 106, the iodine reagent fibers 550, the matrix 660, the iodine reagent fibers 750, or any suitable combination of features of these embodiments. Upon absorption by the water-swellable material, the fluid may come into contact with iodine-forming reagents, and as a result, cause the iodine-forming reagents to be released from the water-swellable material and to come into contact with each other causing an iodine-forming reaction. The resulting iodine that is formed from the reaction may then come into contact with the components of the dressing 882, including the manifold 886. The formed iodine may also be released into the wound or other tissue site, in order to provide its intended antimicrobial functions. In some embodiments, while much of the fluid drawn from a tissue site may be absorbed by the dressing 882, fluid not retained by the dressing 882 may be drawn to the container 890.

Reduced pressure may be applied to the dressing, such as dressing 882, at various times associated with the treatment of a tissue site with an iodine-forming dressing member, such as iodine-forming dressing member 802. For example, in some embodiments, reduced pressure may be delivered to a tissue site prior to the application of the iodine-forming dressing member 802, and thus before the delivery of iodine to the tissue site. In other embodiments, reduced pressure may be applied to a tissue site after the iodine-forming dressing member 802 has been applied to the tissue site, which in some cases may be after iodine has been delivered to the tissue site. Finally, in some embodiments, reduced pressure may be applied to the tissue site while iodine-forming dressing member 802 is applied to the tissue site, and thus while iodine may be being delivered to the tissue site.

The systems, apparatuses, and methods described herein may provide significant advantages, some of which have already been mentioned. For example, the dressing member may improve the controlled release of iodine over time to a wound or tissue site, which may prevent a high uncontrolled dose of iodine from being released. Furthermore, because of these advances, high doses of iodine-forming reagents may be stored in dressings, which may allow the dressings to be applied for longer periods of time or for smaller-sized dressings to be used to deliver the same potential dosage of iodine. Importantly, such dressings may be safer to store, as the elemental iodine is only generated as needed when applied to a wound.

While some exemplary embodiments are described in the context of reduced-pressure therapy applications, many of the features and advantages are readily applicable to other environments and industries.

Although certain illustrative, non-limiting exemplary embodiments have been presented, various changes, substitutions, permutations, and alterations can be made without departing from the scope of the appended claims. Any feature described in connection to any one exemplary embodiment may also be applicable to any other exemplary embodiment.

Further, the steps of the methods described herein may be carried out in any suitable order, or simultaneously where appropriate.

What is claimed is:

1. A system for treating a tissue site, comprising:
   a manifold adapted to receive reduced pressure and distribute the reduced pressure to the tissue site;
   a plurality of iodine-forming reagents adapted to react to form iodine;
   a hollow fiber encapsulating each of the iodine-forming reagents;
   a drape adapted to form a sealed space around the tissue site and the manifold; and
   a reduced-pressure interface adapted to be in fluid communication with the sealed space and the manifold.

2. The system of claim 1, further comprising a dressing member comprising a carrier material and adapted to be disposed proximate the manifold and the tissue site; wherein the plurality of iodine-forming reagents are dispersed in the dressing member.

3. The system of claim 1, wherein the plurality of iodine-forming reagents are dispersed in the manifold.

4. The system of claim 1, further comprising a reduced-pressure source adapted to be in fluid communication with the reduced-pressure interface.

5. The system of claim 1, wherein the manifold is an open-cell, reticulated polyurethane foam.

6. The system of claim 1, wherein the hollow fiber is further adapted to absorb a fluid and to release the iodine-forming reagents.

7. The system of claim 1, wherein the hollow fiber comprises a water-swellable fiber.

8. The system of claim 1, wherein the iodine-forming reagents comprise potassium iodide (KI) and potassium iodate ($KIO_3$).

9. The system of claim 1, further comprising a reduced-pressure delivery tube adapted to be fluidly connected to the reduced-pressure interface.

10. A system for treating a tissue site, comprising:
    a dressing member adapted to be disposed proximate the tissue site and comprising:
       a carrier material, and
       a plurality of iodine-forming reagents adapted to react to produce iodine, the plurality of iodine-forming reagents disposed within a plurality of hollow fibers;
    a drape adapted to cover the dressing member; and
    a reduced-pressure interface configured to be in fluid communication with the dressing member and adapted to deliver reduced pressure.

11. The system of claim 10, wherein the plurality of hollow fibers are adapted to absorb a fluid and to release the iodine-forming reagents.

12. The system of claim 11, wherein the plurality of hollow fibers comprise one or more water-swellable fibers.

13. The system of claim 10, wherein the plurality of iodine-forming reagents comprises potassium iodide (KI) and potassium iodate ($KIO_3$).

14. The system of claim 10, further comprising a reduced-pressure source configured to be in fluid communication with the reduced-pressure interface.

15. A method for treating a tissue site, comprising:
    applying a dressing member to the tissue site, the dressing member adapted to extend beyond the tissue site and overlapping a peripheral surface surrounding the tissue site, wherein the dressing member comprises:

a manifold adapted to receive reduced pressure and distribute the reduced pressure to the tissue site;

a plurality of iodine-forming reagents adapted to react to form iodine;

a hollow fiber encapsulating each of the iodine-forming reagents;

a drape adapted to form a sealed space around the tissue site and the manifold; and a reduced-pressure interface adapted to be in fluid communication with the sealed space and the manifold.

16. The method of claim 15 wherein the plurality of iodine-forming reagents comprises an iodide salt and an iodate salt.

17. The method of claim 15, wherein the iodine is delivered over differing time periods.

18. The method of claim 15, wherein the dressing member further comprises an indicator adapted to provide a blue-black color when exposed to iodine.

19. The method of claim 18, wherein the indicator comprises is a starch.

20. The method of claim 15, further comprising applying reduced pressure to the tissue site.

* * * * *

UNITED STATES PATENT AND TRADEMARK OFFICE
CERTIFICATE OF CORRECTION

PATENT NO. : 10,568,770 B2
APPLICATION NO. : 15/571356
DATED : February 25, 2020
INVENTOR(S) : Timothy Mark Robinson et al.

Page 1 of 1

It is certified that error appears in the above-identified patent and that said Letters Patent is hereby corrected as shown below:

In the Claims

At Column 15, Claim number 19, Line number 22, delete "is" after "comprises".

Signed and Sealed this
Twenty-third Day of June, 2020

Andrei Iancu
*Director of the United States Patent and Trademark Office*